United States Patent [19]
Johansen et al.

[11] Patent Number: 5,432,079
[45] Date of Patent: Jul. 11, 1995

[54] METHOD FOR SELECTING MUTANTS OF LEGUME-NODULATING BACTERIA ENHANCED IN COMPETITION

[75] Inventors: Eric Johansen; Edward R. Appelbaum, both of Madison, Wis.

[73] Assignee: Mycogen Plant Science, Inc., San Diego, Calif.

[21] Appl. No.: 166,681

[22] Filed: Mar. 11, 1988

[51] Int. Cl.$^6$ .......................... C12N 1/20; C12N 1/21; C12N 15/01
[52] U.S. Cl. ...................... 435/252.3; 435/252.2; 435/172.1; 435/172.3; 435/29; 435/34; 435/878; 435/37; 935/76; 935/79
[58] Field of Search .................. 435/29, 34, 37, 172.1, 435/172.3, 878, 252.3, 253, 4.6; 935/76, 79

[56] References Cited

U.S. PATENT DOCUMENTS 4,713,330 12/1987 McLoughlin ......................... 435/34
4,863,866 9/1989 Zablotowicz ..................... 435/172.1

OTHER PUBLICATIONS

Burn et al., "Four Classes of Mutations in the nod D gene of *Rhizobium Seguminosarum* biovar *viciae* that affect its ability to autoregulate and/or activate other nod genes in the presence of other flavonoid inducers", *Genes and Development* vol. 1:456–464, 1987.

Nieuwkoop et al. (1987) J. Bacteriol. 169:2631–2638.
Kosslak et al. (1987) Proc. Natl. Acad. Sci. 84:7428–7432.
Spaink et al. (1987) Nature 328:337–340.
Horvath et al. (1987) EMBO J. 6:841–848.
Burn et al. (1987) Genes and Development 1:456–464.
Hong et al. (1987) Nucl. Acids Res. 15:9677–9690.
McLoughlin, U.S. Pat. No. 4,713,330, issued Dec. 15, 1987.

*Primary Examiner*—Marian Knode
*Attorney, Agent, or Firm*—Saliwanchik & Saliwanchik

[57] ABSTRACT

Methods for the isolation of mutant rhizobial strains with improved competition of nodulation (Comp+) is presented. Mutants are selected for constitutive expression of inducible nod genes (in the absence of inducer) and screened for hyperinduction of nod genes in the presence of inducer. Mutants which are defective in nodulation or in symbiotic nitrogen fixation are eliminated from further testing. Selections for constitutive nod expression and for hyperinduction of nod genes are facilitated by the use of plasmid carrying a selectable marker fused to an inducible nod gene and a plasmid carrying a reporter gene fused downstream of an inducible nod gene. The methods exemplified are particularly useful for the isolation and identification of Comp+ mutants of *Bradyrhizobium japonicum*.

15 Claims, 3 Drawing Sheets

METHOD FOR SELECTING MUTANTS OF LEGUME-NODULATING BACTERIA ENHANCED IN COMPETITION

FIELD OF THE INVENTION

The present invention relates generally to the field of legume-Rhizobium symbiosis, and more particularly relates to a method for the selection and isolation of mutants of nodulating bacteria having improved symbiotic properties.

BACKGROUND OF THE INVENTION

Soil bacteria of the genera Rhizobium and Bradyrhizobium, members of the family Rhizobiaceae, are capable of infecting plants and inducing a highly differentiated structure, the root nodule, within which atmospheric nitrogen is reduced to ammonia by the bacteria. The host plant is most often of the family Leguminosa. Bradyrhizobium, also sometimes designated "slow-growing" rhizobia (Jordan, D.C. (1982) *Int. J. Syst. Bacteriol.* 32:136), includes the commercially important soybean nodulating strains of *Bradyrhizobium japonicum*, the symbiotically promiscuous rhizobia of the "cowpea group," and some strains that can nodulate non-legumes, such as Bradyrhizobium sp. Parasponia. Rhizobium species, also sometimes designated "fast-growing" rhizobia, include among others *R. trifolii* (plant host: clover), *R. meliloti* (plant host: alfalfa), *R. leguminosarum* (plant host: pea). Rhizobium strains generally display a narrow host range.

Within the species *Bradyrhizobium japonicum*, a number of distinct serogroups including, for example, those designated as USDA 123, USDA 110 and USDA 138, are recognized. Strains belonging to the different serogroups have been found to display quantitatively different symbiotic or nodulation properties (Keyser and Griffen (1987) Beltsville Rhizobium Culture Collection Catalogue, U.S. Department of Agriculture). For example, *B. japonicum* USDA 110 are more effective for nitrogen fixation than strains of USDA 123, but USDA 123 strains appear to be more competitive for infection and nodule occupancy than USDA 110 strains.

The process of plant-host recognition, infection and effective nodule formation is complex and involves the coordinated expression of a number of genes in the bacterial symbiont and the host plant. The genetics of the symbiosis and nitrogen-fixation have been the focus of extensive research in recent years in both Rhizobium and Bradyrhizobium strains. Bacterial genes encoding nitrogenase (nif genes), affecting nitrogen fixation in general (fix) and nodule development and, at least in part, host range (nod) have been identified and in many cases located and cloned (see for example recent reviews: Broughton, W. J. (ed.) (1982) *Nitrogen Fixation*, Volumes 2 and 3 (Clarendon Press, Oxford); Puhler, A. (ed.) (1983) *Molecular Genetics of the Bacteria-Plant Interaction* (Springer-Verlag, Berlin); Szalay, A. A. and Legocki, R. P. (eds.) (1985) *Advances in Molecular Genetics of the Bacteria Plant Interaction* (Cornell University Publishers, Ithaca, New York); Long, S. R. (1984) in *Plant Microbe Interactions*, Vol. 1, Kosuge, T. and Nester, E. W. (eds.) (Macmillan, New York) pp. 265-306; Verma, D. P. S. and Long, S. L. (1983) International Review of Cytology (Suppl. 14) Leon, K. W. (ed.) (Academic Press, N.Y.) pp. 211-245).

The nodulation genes and their regulation have been of particular interest in efforts to understand the mechanism of selective infection of particular host plants. A set of genes (nod) associated with a nodulation defective phenotype (NOd+) has been identified on the Sym (symbiotic) plasmids of strains of Rhizobium. The "common" nod genes, designated nodA, B and C, which are associated with the early stages of infection and nodulation, are structurally conserved among Rhizobium strains. In *R. meliloti, R. leguminosarum*, and *R. trifolii*, the nodA, B and C genes are organized in a similar manner and are believed to be coordinately transcribed as a single genetic operon. The DNA region adjacent and 5' to nodA has been found to contain a fourth nodulation gene, designated nodD, which is transcribed divergently from the nodABC operon (Egelhoff et al. (1985) *DNA* 4:241-248; Jacobs et al. (1985) *J. Bacteriol.* 162:469-476; Rossen et al. (1984) *Nucl. Acids Res.* 12:9509-9524). NodD has been found to function in the regulation of expression of nodABC and other nodulation genes (Mulligan and Long (1985) *Proc. Natl. Acad. Sci. USA* 82:6609-6613; Rossen et al. (1985) *EMBO J.* 4:3369-3373; Innes et al. (1985) *Mol. Gen. Genet.* 201:426-432). Comparisons of the DNA sequences and the deduced amino acid sequences of the encoded nodD product confirm the presence of significant sequence conservation of these genes among strains of Rhizobium. NodD mutants in the various species of Rhizobium do not, however, display the same nodulation phenotypes (some are Nod-, and others "leaky" nod- or delayed in nodulation) (Downie et al. (1985) *Mol. Gen. Genet.* 198:255-262; Schofield et al. (1983) *Mol. Gen. Genet.* 192:459-465; Jacobs et al. (1985) *J. Bacteriol.* 162:469-476; Gottfert et al. (1986) *J. Mol. Biol.* 191:411-420). It now appears that many species of Rhizobium carry multiple nodD-like genes, on their Sym plasmids (Rodriquez-Quinones et al. (1987) *Plant Mol. Biol.* 8:61-75; Appelbaum et al. (1985) in *Nitrogen Fixation Research Progress* (Martinus Nijhoff Publishers, Dordrecht, The Netherlands) pp. 101-107; Gottfert et al. (1986) *J. Mol. Biol.* 191:411-420; Appelbaum et al. (1988) *J. Bacteriol.* 170:12-20). Another similarity in the nod region(s) of Rhizobium strains is the presence of conserved sequence elements within the promoter regions of certain inducible nod genes. These conserved sequences, first identified in the nodABC promoter region, are termed the nod-box and are believed to function in induced nod gene expression, possibly as regulatory protein binding sites (Scott et al. (1985) in *Nitrogen Fixation Research Progress*, Evans et al. (eds.), Martinus Nijhoff Publishers, Dordrecht, The Netherlands, p. 130; Rolfe et al. ibid, pp. 79-85; Kondorosi et al. ibid, pp. 73-78).

No Sym plasmids have been associated with Bradyrhizobium strains. The nitrogenase and nodulation genes of these bacteria are encoded on the chromosome. Bradyrhizobium strains contain nodulation genes which are reported to functionally complement mutations in Rhizobium and which show significant structural homology to nodulation gene regions of *R. meliloti* and *R. leguminosarum* (Marvel et al. (1985) *Proc. Natl. Acad. Sci. USA* 82:5841-5845; Russel et al. (1985) *J. Bacteriol.* 164:1301-1308). In *Bradyrhizobium japonicum* strains USDA 110 and 123, nodABC and D gene structural homologs have been identified which are organized in a manner similar to their homologs in Rhizobium strains (Appelbaum, U.S. patent application Ser. No. 875,297, filed Jun. 17, 1986). NodD is read divergently from nodAB and C which are organized in a single operon.

The untranscribed region between nodD and nodA also contains a copy of the conserved nod-box (Appelbaum, U.S. patent application serial number 875,297; Stacy et al. (1987) in *Molecular Genetics of Plant-Microbe Interactions;* Verma and Brisson, (eds.) (Martinus Nijhoff Publishers, Dordrecht, The Netherlands) pp. 197–201). In contrast to Rhizobium strains, *Bradyrhizobium japonicum* strains contain another open reading frame, designated ORF, between nodD and nodA which is believed to be part of the nodABC operon (Appelbaum, U.S. patent application serial number 875,297). A second nodD homolog, nodD2, has been identified in *Bradyrhizobium japonicum* strains USDA 110 and 123, which is positioned about 640 bp downstream from and is transcribed in the same direction as nodD1 (Appelbaum, U.S. patent application Ser. No. 875,297). Both nodD genes may be coordinately transcribed. *B. japonicum* having a mutation in nodD1 only displays a delayed nodulation phenotype, while those having a mutation in nodD2 only show an apparent wild-type nodulation phenotype (see also Nieuwkoop et al. (1987) *J. Bacteriol.* 169:2631). However, mutants carrying a double mutation in both nodD genes display a more pronounced delay than is observed in nodD1 single mutants. The NodD double mutants do, however, remain nod+ (Appelbaum, U.S. patent application Ser. No. 875,297). Other nodD homologs may be present in the *B. japonicum* genome.

It has long been suggested that an exchange of signals between plants and bacteria is requisite for mutual recognition and coordination of the steps of infection and nodulation (Nutman, P. S. (1965) in *Ecology of Soil Borne Pathogens,* eds. F. K. Baker and W. C. Snyder, University of California Press, Berkeley, p. 231–247; Bauer, W. D. (1981) *Ann. Rev. Plant Phys.* 32:407–449; Schmidt, E. E. (1979) *Ann. Rev. Microbiol.* 33:355–376). It is now known, for example, that in both Bradyrhizobium and Rhizobium chemical factors contained in legume exudates induce the expression of nodulation genes.

In Rhizobium the expression of nodABC, nodE and F, and other nodulation genes is reported to be induced in the presence of legume exudates (Mulligan and Long (1985) *Proc. Natl. Acad. Sci.* USA 82:6609–6613; Rossen et al. (1986) *EMBO J.* 4:3369–3373; Innes et al. (1985) *Mol. Gen. Genet.* 201:426–432). Only very low levels of expression of these genes are reported in the absence of exudate. In contrast, nodD expression is reported to be constitutive and not inducible by such exudates. The expression of nodD is reported to be necessary in addition to exudate factors for the expression of the nodABCEFGHI and J genes. In some cases, nodD is reported to regulate its own expression (autoregulation).

The specific components of legume exudate that act to induce nodulation genes in several species of Rhizobium have been identified as flavonoids. Luteolin was reported to be the component of alfalfa exudates that induces nod ABC expression in *R. meliloti* (Peters et al. (1986) *Science* 233:977–980) Three clover exudate constituents: 4',7-dihydroxyflavone, geraldone and 4'-hydroxy-7-methoxyflavone were reported to induce the nodulation genes of *R. trifolii* (Redmond et al. (1986) *Nature* 323:632–635). Two pea exudate components: eriodictyol, and apigenin-7-O-glucoside were reported to induce the nodulation genes of *R. leguminosarum* (Firmin et al. (1986) *Nature* 324:90–92; Zaat et al. (1987) *J. Bacteriol.* 169:198–209). In addition, molecules having structures related to those of the inducer found in exudate were assessed for their ability to induce. Inducers of Rhizobium nodulation genes appear in general to be limited to certain substituted flavonoids, and the range of compounds to which a Rhizobium responds is species specific. Since host range is used to classify Rhizobium strains into different species, this suggests that differential response to inducer molecules is involved in the mechanism of determination of host range.

Two isoflavone components of soybean exudate, daidzein and genistein, have been reported to be inducers of the nodulation genes of *B. japonicum* strains 110 and 123 (Kosslak et al. (1987) *Proc. Natl. Acad. Sci.* USA 84:7428–7432. Several other isoflavones were found to be inducers (7-hydroxyisoflavone, 5,7-dihydroxyisoflavone and biochanin A) or weak inducers (formononetin and prunetin) of the *B. japonicum* nod genes In addition, two flavones: 4',7-dihydroxyflavone and apigenin which induce certain Rhizobium nod genes were also found to induce the *B. japonicum* nod genes. It is interesting to note that isoflavones were reported to be antagonists of induction of nodulation genes of Rhizobium strains (Firmin et al. (1986) *Nature* 324:90–92).

It has been reported that nodulation host specificity is at least in part mediated by a selective interaction of host plant factors with the specific nodD gene(s) of a particular rhizobium to stimulate nod gene expression and effect nodulation (Spaink et al. (1987) *Nature* 328:337–340; Hong et al. (1987) *Nucl. Acids Res.* 15:9677–9690). While the nodD genes of various rhizobia have significant homology, they are much more conserved in the amino-terminal portion than in the carboxy-terminal portion of the coding region. Any functional differences between nod gene products is expected to reside in the carboxy-terminal portion of the protein. Horvath et al. (1987) *EMBO J.* 6:841–848 have reported the construction of a chimeric nodD gene having the 5'-end of the nodD1 of a broad host range Rhizobium which nodulates the tropical legume siratro (MPIK3030) and the 3'-end of the nodD1 of *R. meliloti*. When this chimeric gene was introduced into a nodD$^-$ double mutant (both nodD genes inactivated) of *R. meliloti,* the transconjugant nodulated alfalfa normally. When this chimeric gene was introduced into a nodD' mutant of MPIK3030, the transconjugant strain did not nodulate siratro.

Burn et al. (1987) *Genes & Development* 1:456–464 also link nodD to the inductive response to inducer as well as antagonist (or anti-inducer) molecules. They report nodD mutants of *Rhizobium leguminosarum* that are affected in their ability to activate nod gene expression in response to inducer molecules. One class of mutants described, designated class IV, are reported to display nod gene induction in the absence of inducer molecules and enhanced levels of nod gene induction in the presence of inducer; what is herein designated as a hyperinducible phenotype. In addition, this class of mutants also displayed altered response to molecules which were antagonists of induction in the wild-type parent strain. However, class IV nodD mutants were reduced in nodule number compared to the wild-type and, furthermore, they did not fix nitrogen (fix$^-$). These mutants contained a single C to T transition in the nodD coding sequence, substituting an asparagine for an aspartic acid in the nodD protein. Other nodD mutant classes affected either in autoregulation or the ability to activate nod gene induction, or both, were also described. It is suggested that the overproduction of the inducible nod gene in class IV mutants is deleterious to nodulation, resulting in decreased nodule number and ability to fix nitrogen. The *Rhizobium leguminosarum* nodD mutants described by Burn et al. (1987) supra were isolated by induced mutagenesis of plasmids containing nodD. The mutagenized nodD plasmids were then introduced into *R. leguminosarum* strains which lacked a Sym-plasmid and contained either a nodC- or nodD-lacZ fusion. Mutants affected in induction response were screened employing expression of β-galactosidase to assess nod gene induction.

SUMMARY OF THE INVENTION

It is an object of this invention to provide mutants of legume-nodulating bacteria which are enhanced in competition for nodule occupancy compared to their parent strain. These Comp+ or competition enhanced mutants are useful as components of improved legume inoculating compositions.

To accomplish this object a method for selecting and isolating competition enhanced mutants of legume-nodulating bacteria is provided. The method generally involves the initial screening of a mutant population of a legume-nodulating bacterium for hyperinducible mutants. After selection and isolation of a set of hyperinducible mutants, the mutants are assessed for their ability to form nitrogen fixing nodules on their host legume. Those mutants that are Fix− are eliminated from further screening. The remaining Fix+ hyperinducible mutants are then assessed for nodule competition and compared to the parent legume nodulating strain and those that are enhanced in competitive ability with respect to the parent are selected.

In general any method of screening or selecting for hyperinducible mutants can be employed. For example, hyperinducible mutants can be screened employing an inducible nod gene-reporter gene fusion to assess reporter gene expression levels in mutants. Alternatively, a selection/screening method employing an inducible nod gene-selectable marker gene fusion and a screen or assay for hyperinducible mutants can be used. More specifically, this selection for hyperinducible mutants involves the following steps:

i. introducing a selection plasmid into a legume-nodulating bacterium, wherein the selection plasmid comprises an inducible nod gene-selectable marker gene translational fusion, to obtain a selectable parent transconjugant strain of the legume-nodulating bacterium;

ii. selecting mutants of the parent transconjugant strain which constitutively express the phenotype of the selectable marker gene independently of the presence of a nod gene inducer molecule in their growth medium, to obtain a set of mutants;

iii. eliminating from the set of mutants those mutants in which the constitutive selectable phenotype is caused by a mutation on the selection plasmid or a plasmid copy number mutation and also eliminating those mutants which retain the selectable phenotype when cured of the selection plasmid, to obtain a subset of mutants;

iv. screening the subset of mutants for those mutants that have a hyperinducible nodulation phenotype, to obtain a set of hyperinducible mutants of the legume-nodulating bacterium.

In a specific embodiment the screening for hyperinducible mutants is accomplished by the following steps:

a. initially curing the mutants of the subset of mutants of the selection plasmid, followed by b. introducing into the cured mutants an assay plasmid which comprises an inducible nod gene-reporter gene fusion, and c. selecting those mutants which display a higher level of basal and induced expression of the reporter gene compared to the level of reporter gene expressed by the parent legume-nodulating strain, to obtain a set of hyperinducible mutants.

The methods of the present invention are generally applicable to legume-nodulating strains including strains of both Rhizobium and Bradyrhizobium, and are particularly applicable to strains of *Bradyrhizobium japonicum*. These methods can be employed to screen for spontaneous mutations, for induced mutations or for mutations introduced by recombinant methods. In general, any selectable marker gene can be employed as long as the gene product is functional and the phenotype conferred by the gene is selectable in the legume-nodulating bacterium. Similarly, any reporter gene can be employed as long as the expression of the reporter gene can be assayed in the legume-nodulating bacterium. The regulatory sequences of any legume-exudate inducible nod gene of a legume-nodulating bacterium can be employed in the gene fusions of the present invention. Gene-fusions within the nodABC transcriptional unit are particularly useful.

The methods of the present invention can be used to reproducibly select for and isolate Comp+ mutants of legume-nodulating bacteria including Comp+ mutants of Bradyrhizobium and Rhizobium strains. In particular, these methods are useful for isolating Comp+ mutants of strains of *Bradyrhizobium japonicum*. The Comp+ mutants of *Bradyrhizobium japonicum*, particularly those of USDA 110, are useful as components of soybean inoculating compositions.

The present invention provides hyperinducible mutants of legume-nodulating bacteria, including mutants of Bradyrhizobium and Rhizobium, which are also enhanced in competition for nodulation. These mutants can be spontaneous mutants, induced mutants or mutants obtained by recombinant methods. In a specific embodiment, the present invention provides the competition enhanced mutant *B. japonicum* USDA 110 strain 46c1.

Restriction sites are indicated as: Hp=HpaI; H=HindII; Bg=BglII; Bc=BclI; S=SalI and E=EcoRI.

Figure 2:
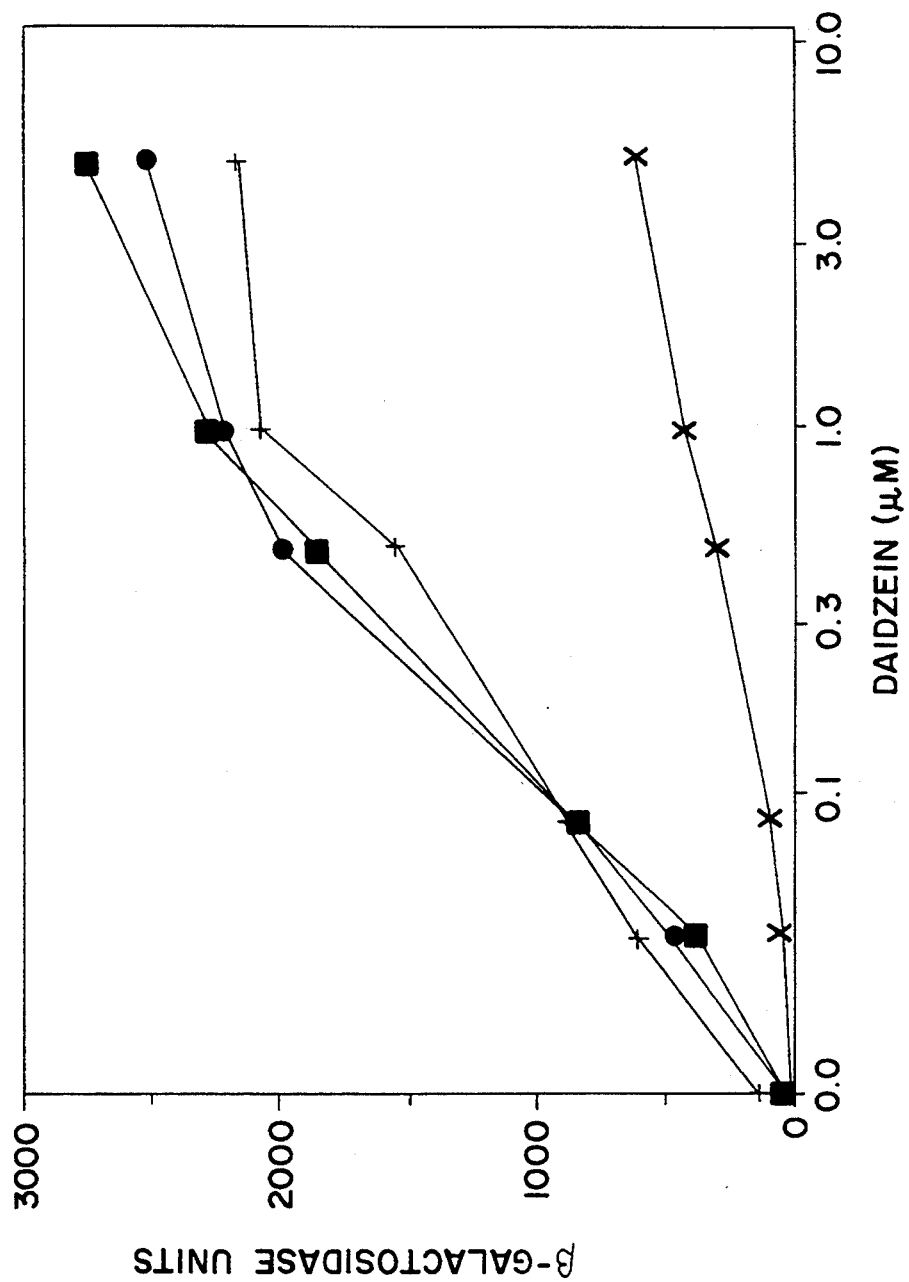

FIG. 2 is a graph comparing the inductive response of the B. japonicum 110 mutants and parent 110spc containing pEA2-21 on exposure to varying concentrations of inducer, daidzein. Induction response is measured in β-galactosidase units, as described in Example 3, as a function of daidzein concentration (μM). Induction in the parent 110spc(pEA2-21) is indicated by (X), mutant 31c1(pEA2-21) by closed squares (■), mutant 32c1(pEA2-21) by crosses (+) and mutant 46c1(pEA2-21) by closed circles (●).

Figure 3:
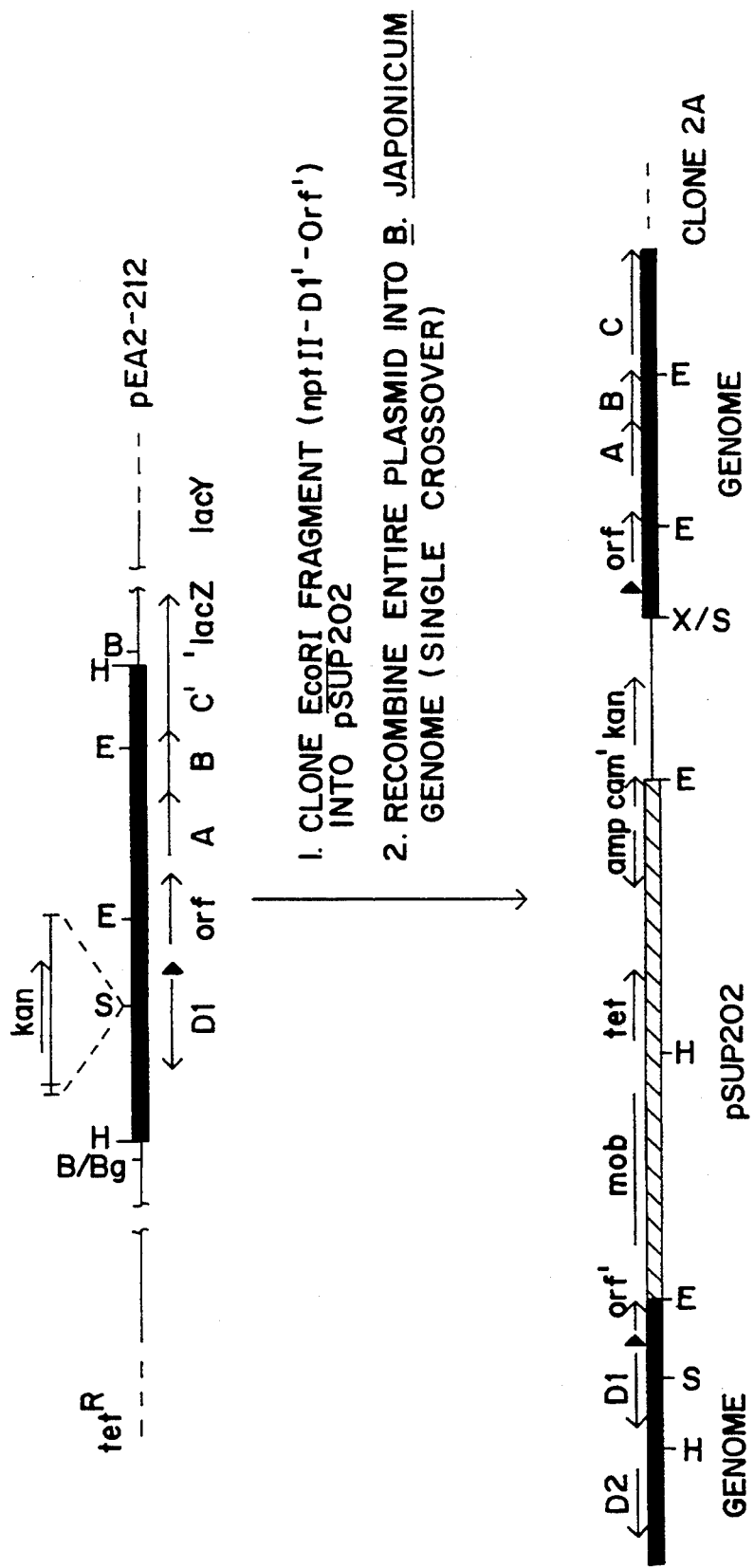

FIG. 3 is a schematic diagram, not necessarily drawn to scale, of the insertion of the Tn5 derived DptII gene and promoter into the B. japonicum USDA 110 genome to produce clone 2A having constitutive expression of the nodABC genes. A restriction diagram of pEA2-212 containing the nptII gene insert into pEA2-21 is shown. An EcoRI fragment of pEA2-212 containing nodD1-ORF region containing the inserted nptII is excised, inserted in pSUP202 and introduced into the genome by recombination. A restriction diagram of the relevant portion of the B. japonicum USDA 110 clone 2A is provided. Restriction sites are indicated as: E=EcoRI; H=HindIII; B=BamHI; X=XhoI; S=SalI; Bg=BglII.

DETAILED DESCRIPTION OF THE INVENTION

Competition (Comp+ or Comp−) as used herein refers to a mutant phenotype of the root nodulating bacteria of the genera Rhizobium and Bradyrhizobium associated with the ability of the root nodulating strain to compete with other strains in the formation of nodules on a host plant. Relative competitive ability can only be assessed between two strains when they nodulate the same host plant. The effect of competition between root nodulating strains is manifested when nodule occupancy (measured as the percent of total nodules occupied by a given strain) is not directly proportional to the composition of the inoculum. For example, if a host plant is inoculated with an inoculum containing equal numbers of two strains A and B, the two strains are equal in competitiveness if each strain occupies 50% of the nodules of the host plant; strain A is more competitive than B if A occupies more nodules than B; and strain B is more competitive than A if B occupies more nodules than A. Two mutant phenotypes, Comp+ and Comp−, referring respectively to enhanced competitive ability and reduced competitive ability with respect to the parent or wild-type strain are defined herein. Differences in competitive ability can be due to auxotrophy or to changed growth properties of a strain. The Comp+ mutants of the present invention appear to have growth properties similar to those of their parent.

Hyperinducibility as used herein refers to a mutant phenotype of nodulating bacteria whose legume-exudate inducible nod genes (i.e. nodAB and C) are induced to a higher level of expression in the presence of a nod gene inducer molecule than are those of the wild-type. Hyperinducibility is assessed herein by measuring the expression level of a nod gene-reporter gene fusion, a nodC-lacZ gene fusion, in a mutant strain compared to the its expression in the parent strain. Hyperinducible mutants also display enhanced constitutive (non-induced) levels of nod gene expression. Burn et al. (1987) supra have previously described hyperinducible mutants of R. leguminosarum, which are, in addition, deficient in nodulation (lower nodule number) and which do not fix nitrogen (Fix−). Three types of Bradyrhizobium japonicum hypernodulation mutants have been characterized in the present work. The first type, exemplified by mutant 32c1, is apparently similar to the mutants reported by Burn et al. (1987) supra being Fix− when inoculated on soybean. Mutant 32c1 does, however, produce a normal number of nodules. The second type, exemplified by mutant 31c1, is Fix+ when inoculated on soybean. The third type, exemplified by mutant 46c1, is also Fix+ but is distinguished from mutant 31c1 in having a changed inductive response to certain flavones. More importantly, the third type of hyperinducible mutant was found to be enhanced in competitive ability compared to its parent (Comp+) for nodulation on soybean. The first and second type of hyperinducible mutants are impaired in competitive ability compared to their parent (comp−).

The term selectable plasmid is used specifically herein to refer to a plasmid which contains a gene which confers a selectable phenotype which has been placed under the control of the regulatory sequences of an inducible nod gene of a legume-nodulating bacterium. The selectable plasmid must be capable of being introduced and stably maintained in the legume-nodulating bacterium and the phenotype conferred must be selectable in the legume-nodulating bacterium. The selectable marker gene, for example an antibiotic resistance gene, can be placed under the control of the inducible nod gene regulatory sequences, for example, by construction of a nod gene-selectable marker gene translational fusion, such as that in kan6, in which a B. japonicum nodC gene is fused to a fragment containing the kan, str and ble genes of Tn5.

The term inducible nod gene refers to those nodulation genes of a legume-nodulating bacterium whose expression is induced by components of legume exudates. These nod genes can also be referred to as legume-exudate inducible nod genes. In particular, the nodABC operon of Rhizobium and Bradyrhizobium strains is expressed in response to legume exudates. Other inducible nod genes include nodEFGHI and J genes. A number of nod gene inducer molecules of Rhizobium and Bradyrhizobium japonicum strains have been identified. Inducers of Rhizobium nod genes are reported to be limited to certain flavonoid compounds, while B. japonicum nod genes are induced by certain flavonoids and isoflavonoids. For example, the isoflavones daidzein and genistein act as inducers of the B. japonicum nod genes. Expression of the inducible nod genes also requires a functional nodD gene.

The term assay plasmid is used specifically herein to refer to a plasmid which contains a reporter gene whose expression can be quantified which is placed under the control of the regulatory sequences of an inducible nod gene of a legume-nodulating bacterium. The assay plasmid must be capable of being introduced into and stably maintained in the legume-nodulating bacterium. The reporter gene is one whose expression level can be measured, for example the lacZ gene. Expression of the reporter gene can be quantified in visual, chemical, immunological, hybridization or other assays. For example, the expression of the β-galactosidase is readily measured as described in Example 4. β-galactosidase activity can be readily assessed in visual plate assays which are useful in the screening of large numbers of bacteria. The reporter gene can be placed under the control of the inducible nod gene regulatory sequences, for example, by construction of a nod gene-reporter gene fusion, such as that in pEA2-21, in which a *B. japonicum* nodC gene is fused to a lacZ gene.

The present invention provides a screening/selection method for isolating mutant legume nodulating bacteria which are enhanced in competitive ability compared to their parent. The method is based on the discovery that certain hyperinducible mutants of legume nodulating bacteria are also enhanced in competitive ability. Prior to this discovery there was no reason to associate the phenotype of hyperinducibility with enhanced competitiveness. In fact, previous reports associated the hyperinducible phenotype of legume nodulating bacteria with impaired symbiotic properties and lack of ability to fix nitrogen.

In general, the method of the present invention employs an initial screening of a mutant population of a legume-nodulating bacterium for hyperinducible mutants. The hyperinducible mutants are selected and isolated and then assayed individually for nodulation properties and competition. Those hyperinducible mutants which are Fix− are eliminated from further screening. The remaining hyperinducible mutants are assayed in planta for enhanced competitive ability compared to the parent strain.

More specifically, the method of the present invention employs a plasmid containing a nod gene-selectable marker gene transcriptional fusion, such as the nod gene-antibiotic resistance gene fusion of kan6 (FIG. 1) which is introduced into a parent strain and used to select for mutants in which the selectable fusion gene is expressed in the absence of a nod gene inducer molecule. Intermediate screening steps eliminate those mutants in which the selectable phenotype is associated with a mutation on the selection plasmid, plasmid rearrangements, plasmid copy number increase, or introduction of the selectable marker gene into the genome (which in Rhizobium includes the Symplasmid). The mutants that remain after these intermediate screens will carry mutations on the genome. The nod gene induction response of the remaining mutants is then measured employing a plasmid containing a nod gene-reporter gene fusion, such as a nod gene-lacZ fusion. Those mutants that are hyperinducible, i.e., those having enhanced basal and inducible levels of nod gene expression, are selected. The selected hyperinducible mutants are screened in planta for defects in symbiotic properties, for example, those that are Fix− are eliminated. Finally, the competitive ability of the remaining mutants compared to their parent strain is determined in competition assays on host plants.

The method of the present invention can be employed generally to isolate Comp+ mutants of strains of Bradyrhizobium or Rhizobium. As will be appreciated by those in the art, appropriate adjustments of the nod-gene fusions employed for selection and induction assays and the nod-gene inducer molecules, for example, must be made for application of the methods to the various species of rhizobia.

The enhanced competition mutants (Comp+) of nodulating bacteria isolated by the methods described herein are useful as components in improved legume inoculants in which, for example, the inoculant bacteria is improved in competitiveness with respect to the indigenous population of rhizobia. It will also be understood that the Comp+ mutants of the present invention can be employed in the preparation of improved nodulating strains in which further enhancement of the symbiotic properties are introduced by genetic manipulation, for example a Comp+ mutant may be made more efficient in nitrogen fixation.

The method of the present invention has been exemplified by the isolation of spontaneous Comp+ mutants of *B. japonicum* USDA 110. Specifically, a *B. japonicum* nodC-streptomycin resistance gene transcriptional fusion was prepared (kan6) and introduced into a spectinomycin resistant *B. japonicum* USDA 110 parent strain. *B. japonicum* spc 110(kan6) was then plated ($10^5$–$10^6$ bacteria/plate) on selective medium containing a high level of streptomycin (1375 μg/ml) and streptomycin resistant spontaneous mutants were isolated. A total of 43 mutants were obtained. A summary of the mutant classes obtained in this screen is presented in Table 1.

TABLE 1

Summary of mutant classes obtained following selection of $STR^R$ from 110 spc(kan6)

Class I
Plasmid copy number mutants (16/43 of mutants selected)

Characteristics:
(a) pEA2-21(kan6) cannot be cured
(b) plasmid bands on Southern blot more intense than in parent Class II
Chromosomal str mutations (2/43 mutants)

Characteristics:
(a) plasmid already lost, so 100% cured
(b) no plasmid bands in Southern blot
(c) cured strains streptomycin-resistant
(d) cured strains with pEA2-21 identical to 110 spc(pEA2-21) in β-galactosidase activities with or without inducer Class III
Plasmid rearrangements (6/43 mutants)

Characteristics:
(a) cured like parent strain
(b) Southern blot reveals novel bands
(c) cured strains streptomycin-sensitive
(d) cured strains with pEA2-21 identical to 110 spc(pEA2-21)

Class IV
Plasmid mutations (16/43 mutants)

Characteristics:
(a) cured like parent strain
(b) plasmid bands in Southern blot identical to parent
(c) cured strains streptomycin-sensitive
(d) cured strains with pEA2-21 had levels of β-galactosidase identical to those of 110 spc (pEA2-21)

Class V
Hyperinducible mutants (3/43 mutants)

Characteristics:
(a) cured like parent strain
(b) plasmid bands in Southern blot identical to parent
(c) cured strains streptomycin-sensitive
(d) cured strains with pEA2-21 had elevated basal levels of β-galactosidase as well as elevated induced levels compared to 110 spc(pEA2-21)

Class I plasmid copy number mutants and Class II plasmid rearrangement mutants were identified by Southern blot analysis of DNA preps. Alteration in plasmid size were ascertained in SnaBI digested mutant DNA preps and changes in plasmid copy number were ascertained by comparisons of the intensities of appropriate plasmid DNA bands. Mutants in classes I and III were eliminated from further screening.

The remaining mutants were cured of the selection plasmid. Those cured mutants that remained streptomycin-resistant were classified into class II, chromosomal str mutants, and eliminated from further screening.

The remaining streptomycin-sensitive cured mutants were further classified according to their inductive response to nod gene inducers. Inductive response was assessed by introducing nodC-lacZ fusion plasmid, pEA2-21, into the plasmid cured mutants, and measuring $\beta$-galactosidase expression with and without inducer, in this case daidzein, present. Expression of pEA2-21 in the mutants was compared to that in the parent 110spc strain. Those mutants having no difference in expression of the nodC-lacZ fusion compared to the parent were classified into class IV, as having had mutations on the selection plasmid which affected expression of the plasmid borne str gene. The remaining mutants were classified into class V as having genomic mutations. Due to the nature of the selections employed, the class V mutations must affect the expression or functioning of a trans-acting factor, such as regulatory protein.

Three class V mutants were identified, the plasmid-cured derivatives of which have been designated, 31c1, 32c1 and 46c1. FIG. 2 is a graph comparing the expression of the pEA2-21 nodC-lacZ fusion in the three class five mutants and the parent USDA 110spc as a function of the concentration ($\mu$M) of daidzein. In all three mutants the nod fusion is expressed to a higher level than in the parent strain. Table 2 shows the uninduced and induced (at 5 $\mu$M daidzein) levels of expression of $\beta$-galactosidase in the three mutants and the parent. All three mutant strains display enhanced levels of constitutive expression of the nod fusion compared to the parent strain. Mutant 32c1 appear to have a significantly higher constitutive level of expression compared to the other two mutants. All three USDA 110 class V mutants isolated have a hyperinducible phenotype.

TABLE 2

| Strain | $\beta$-galactosidase activity of 110 parent mutants. | |
|---|---|---|
| | Uninduced | Induced |
| 110 spc(pEA2-21) | 26 | 644 |
| 46 cl(pEA2-21) | 44 | 2670 |
| 31 cl(pEA2-21) | 61 | 2570 |
| 32 cl(pEA2-21) | 153 | 2160 |

Table 3 compares the relative induction response of the three mutants and the parent 110 strain in response to a number of flavonoid and isoflavonoid nod gene inducers (at 5 $\mu$M). The pattern of induction is similar for all three mutants except that mutant 46c1(pEA2-21) is induced to a higher level than the other two mutants in response to genistein, biochanin A, formononetin and 4',7-dihydroxyflavone.

The nodulation properties of the three USDA 110 class V mutants were assessed by inoculation on soybean. As shown in Table 4, all three mutants produced a normal-number of nodules compared to the parent strain. One of the mutant strains, 32c1, did not fix nitrogen resulting in yellow stunted plants.

The results of competition assays of the parent 110spc and the class V mutants vs. B. japonicum 110str are presented in Table 5. Note that the mutants are SPC[R] spontaneous mutants like their parent strain 110spc. Three inoculum compositions, having approximate inoculum ratios of 2:1, 1:1 and 1:2 (SPC[R] strain/STR[R] strain) were inoculated onto soybeans and nodule occupancy was determined. At all three inoculum ratios, mutant 46c1 is more competitive than its parent 110spc against 110str, although this is most clearly demonstrated in the results

TABLE 3

| | $\beta$-galactosidase activity with various inducers[a,b] | | | |
|---|---|---|---|---|
| Inducer | 110 spc[a] | 31 | 32 | 46 |
| Ethanol | 11 | 75 | 166 | 45 |
| Daidzein | 391 | 1620 | 1640 | 1790 |
| Genistein | 193 | 1500 | 1420 | 2280 |
| Biochanin A | 31 | 368 | 277 | 2060 |
| Formononetin | 68 | 612 | 543 | 1150 |
| Apigenin | 7 | 56 | 104 | 71 |
| Chrysin | 17 | 75 | 170 | 74 |
| Narigenin | 21 | 76 | 187 | 94 |
| Kaempferol | 52 | 184 | 353 | 167 |
| Coumestrol | 176 | 866 | 942 | 738 |
| Dimethylformamide | 20 | 74 | 211 | 59 |
| 4',7-Dihydroxyflavone | 24 | 112 | 299 | 625 |

[a]All strains contain plasmid pEA2-21, the nodC-lacZ fusion plasmid.
[b]The concentration of inducer employed in each case was 5 $\mu$M. Inducers were added as ethanolic solutions, or in the case of 4',7-Dihydroxyflavone, as a solution in dimethylformamide.

TABLE 4

| | Nodulation properties of mutants and wild-type[a] | | |
|---|---|---|---|
| Strain | Nodules per plant | Nodule Mass (mg per nodule) | Fixation Phenotype |
| 110 spc | 41.7 ± 9.5 | 10.6 ± 1.4 | fix+ |
| 31 cl | 45.7 ± 12.9 | 10.5 ± 2.6 | fix+ |
| 32 cl | 53.2 ± 11.0 | 5.2 ± 0.9 | fix− |
| 46 cl | 35.4 ± 9.1 | 10.9 ± 2.9 | fix+ |

[a]Inoculum contained about 2 × 10⁵ rhizobium.

TABLE 5

| Competition of 110 spc and mutants against 110 str[a] | | | | |
|---|---|---|---|---|
| | Actual ratio | % occupancy by | | |
| | | spc | str | mixed |
| | 2:1 ratio | | | |
| 110 spc | 1.98:1 | 83 | 10 | 5 |
| 31 cl | 2.13:1 | 63 | 25 | 11 |
| 32 cl | 2.70:1 | 0 | 98 | 2 |
| 46 cl | 1.78:1 | 89 | 5 | 5 |
| | 1:1 ratio | | | |
| 110 spc | 1.12:1 | 61 | 25 | 12 |
| 31 cl | 1.02:1 | 37 | 48 | 14 |
| 32 cl | ND[b] | | | |
| 46 cl | 0.88:1 | 85 | 8 | 7 |
| | 1:2 ratio | | | |
| 110 spc | 1:1.93 | 48 | 39 | 13 |
| 31 cl | 1:2.36 | 27 | 56 | 16 |
| 32 cl | 1:2.30 | 0 | 100 | 0 |
| 46 cl | 1:1.91 | 82 | 13 | 3 |

[a]Total inoculum contained about 2 × 10⁵ rhizobium.
[b]ND = Not Determined.

of the 1:1 and 1:2 ratio assays. The results of these experiments indicate that mutants 31c1 and 32c1 are less competitive than their parent 110spc strain.

In related work, a recombinant B. japonicum USDA 110spc in which the nodABC genes were placed under the control of constitutive promoter sequences was constructed. In this strain designated clone 2A, a DNA fragment of Tn5 containing the nptII coding region and promoter sequences was inserted into the B. japonicum 110spc genome by recombination such that it was positioned upstream from the nodORFABC operon and such that the nptII sequences were oriented in the same direction as ORF and the nodABC genes (see FIG. 3). This recombinant strain was assessed for competitive ability compared to its parent USDA 110spc, in order to determine the effect of constitutive expression of the nodABC genes on competition for nodulation. The recombinant mutant 2A had nodulation properties similar to its parent and was Fix+. The results of the competition experiments are shown in Table 6. The recombinant mutant 2A is significantly less competitive than its 110spc parent. These results indicate that constitutive expression of the nodABC genes, as in mutant 2A, does not necessarily lead to enhanced competitive ability, but can be detrimental to competitive ability.

TABLE 6

Effect of Constitutive nodABC Expression on Competitiveness of 110 spc

| 1:1 ratio | | % Nodules Containing | | |
|---|---|---|---|---|
| $5 \times 10^4$ | $4 \times 10^4$ | $SPC^R$ | $STR^R$ | MIXED |
| 110 spc | 110 str | 68 ± 5 | 21 ± 8 | 11 ± 6 |
| 110 spc-2A | 110 str | 6 ± 5 | 91 ± 9 | 3 ± 4 |
| 1:10 ratio | | | | |
| $5 \times 10^4$ | $4 \times 10^5$ | | | |
| 110 spc | 110 str | 13 ± 11 | 81 ± 17 | 6 ± 10 |
| 110 spc-2A | 110 str | 1 ± 2 | 99 ± 2 | 0 ± 0 |

EXAMPLES

Example 1

Construction of nodC-lacZ Fusion Plasmid pEA2-21.

Clones and subclones containing the nod region of *B. japonicum* USDA 123 were obtained as described previously (Appelbaum et al., U.S. patent application Ser. No. 875,297). Briefly, a *B. japonicum* USDA 123 cosmid gene bank was prepared. Total genomic USDA 123 DNA was prepared as in Scott (1981) *J. Mol. Appl. Genet.* 1:71–81, and partially digested with EcoRI. Digested DNA was then fractionated on a sucrose gradient to isolate DNA fragments ranging in size from 12–50 kb. These DNA fragments were ligated to EcoRI digested pLAFR1 (Freedman et al. (1982) *Gene* 18:289–296). The ligated DNA was packaged into phage heads using conventional techniques and introduced into *E. coli* strain HB101. A total of 6200 cosmids were saved for screening. This cosmid bank of *B. japonicum* DNA was screened for cosmids capable of hybridizing to a 2 kb BamHI/HindIII fragment of pRmSL42 that contains the nodAB and C sequences of *R. meliloti* (Egelhoff et al. (1985) *DNA* 4:241–248). One strongly hybridizing cosmid was found which contained a 1.6 kb EcoRI fragment that was subsequently shown to contain *B. japonicum* nod A and B sequences. The insert of the selected cosmid was then employed to rescreen the cosmid bank for larger inserts. One cosmid, designated pEA71-1A, selected by this screen was picked, repurified and the approximately 30 kb cosmid insert was subjected to restriction analysis. Digestion of this cosmid with EcoRI resulted in several EcoRI subfragments, including a 1.6 kb fragment which hybridized to the 1.6 kb EcoRI fragment obtained by direct screening (vide supra) and a 3.6 kb fragment which hybridized to a 3.0 kb nodD probe which contained the nodD-r2 gene of *R. fredii* USDA 191 (Appelbaum, U.S. application Ser. No. 763,939). Southern blot analysis using several restriction enzymes indicated that these two fragments were adjacent to each other in the large cosmid insert. The nod region of *B. japonicum* USDA 123 is contained in this cosmid insert. The positions and orientations of nod genes within this region were confirmed by DNA sequencing and are shown in FIG. 1.

Example 2

Construction of nodC-kan-str Transcriptional Fusion Plasmid, pEA2-21 kan6.

Figure 1:
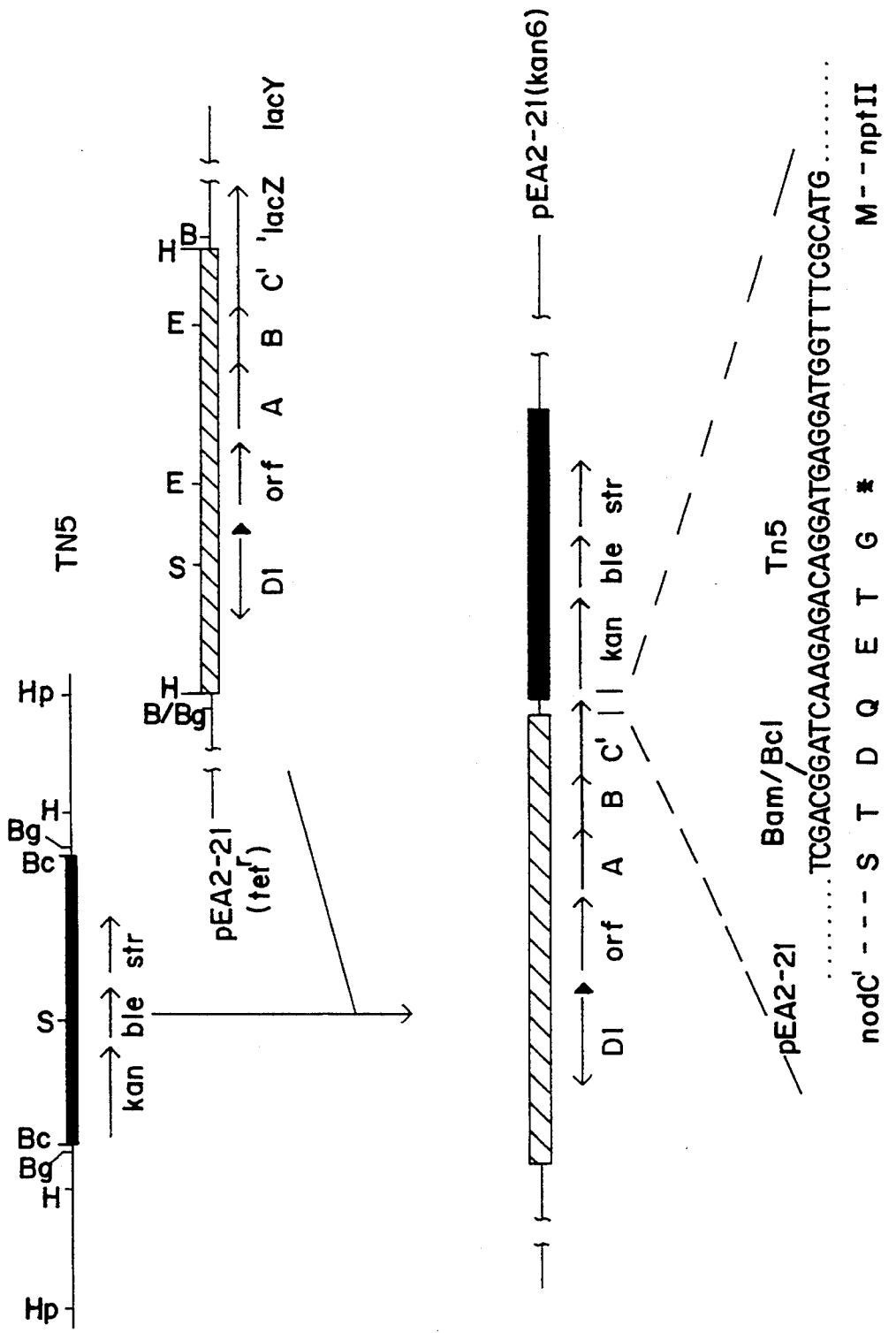
FIG. 1 is a schematic diagram, not necessarily drawn to scale, of the construction of the selection plasmid pEA2-21(kan6), also designated kan6. A restriction endonuclease map of the relevant portion of the transposon Tn5 is shown (Jorgenson et al. (1979) *Mol. Gen. Genet.* 177:65–72), indicating the BclI fragment and the locations of the kan, ble and str resistance genes therein. Also shown is a restriction map of the relevant portion of the pGD926 derivative nodC-lacZ fusion plasmid, pEA2-21 (Kosslak et al. (1987) *Proc. Natl. Acad. Sci. USA* 84:7428–7432) indicating the locations of the nodD1, A, B and the nodC-lacZ fusion as well as the locations of the ORF and nod-box, which is indicated as a solid triangle in the nodD1-ORF intergenic region. The BclI fragment of Tn5 is inserted into the BamHI sits in the nodC-lacZ fusion of pEA2-21 to give the selection plasmid kan6. The locations of the nod genes and antibiotic resistance genes in kan6 are indicated. The DNA sequence in the region of the gene fusion in kan6 is provided and the termination codon about 12 bases 5′ to the nptII initiation codon is indicated (*).

A BclI fragment from Tn5 (FIG. 1, Jorgenson et al. (1979) *Mol. Gen. Genet.* 177:65–72), containing the genes for three drug resistances (kanamycin (nptII), bleomycin and streptomycin) but containing no known promoter sequence was cloned into the BamH1 site of the nodC-lacZ fusion plasmid pEA2-21 (FIG. 1). This new plasmid was designated pEA2-21(kan6) and is herein referred to as kan6.

The BclI fragment was inserted in kan6 in such a way that the drug resistance genes would be transcribed and translated in the same direction as the nodABC genes. Translation of the nodC coding region stops 15 base pairs before the initiation codon of neomycin phosphotransferase II gene of the inserted fragment (see FIG. 1).

Plasmid kan6 was transferred to *Bradyrhizobium japonicum* strain 110spc by conjugation. *B. japonicum* 110spc(kan6) was resistant to high levels of kanamycin (2000 μg/ml) regardless of whether or not daidzein, a *B. japonicum* nodABC gene inducer, was present in the medium. Similarly, *B. japonicum* 110spc(kan6) was resistant to typically inhibitory levels of streptomycin (about 250 μg/ml) in the presence or absence of inducer. These results indicated that both the kan and str resistance genes were constitutively expressed in the kan6 construction most likely by promoter sequences in the plasmid. Experiments performed using much higher levels of streptomycin (greater than 1,000 μg/ml) showed that growth of *B. japonicum* 110 spc(kan6) was stimulated by inducer in the presence of the antibiotic. This indicated that expression of streptomycin resistance was inducible, and that the antibiotic resistance gene was also under the control of the nod gene regulatory system. Using ELISA methods with anit-nptII antibodies, it has been determined that the gene of kan6 is induced about 25-fold by inducer. The nptII gene (kan) is therefore also under the control of the nod gene regulatory system, however this was not detected employing the kanamycin plate selection assays.

Example 3

Selection of Competition Mutants

Spontaneous mutants of *B. japonicum* 110spc(kan6) resistant to streptomycin in the absence of inducer daidzein were isolated by streaking (approximately $10^6$ bacteria) on Ag medium containing 1375 μg/ml streptomycin. Mutants were purified and maintained on Ag medium containing 1000 μg/ml streptomycin. To ensure selection of independent isolates only one mutant/streak was picked. Ag medium is the same as AIEHM medium of Kuykendall (1979) *Appl. Environ. Micro.* 37:862–866. Five classes of $STR^R$ mutants, as described in Table 1 were identified. The identifying characteristics of the mutant classes are listed in Table 1. A total of 43 mutants were isolated.

Mutants were initially characterized using DNA preps and Southern blots to determine the general nature of the mutations. As there is no reliable procedure for the preparation of plasmid DNA from Bradyrhizobium, the presence and nature of any plasmids present is ascertained using Southern blot techniques of whole cell DNA. The kan6 plasmid is cleaved into two fragments (about 12 kb and about 23 kb) by the restriction enzyme SnaBI. The presence of the plasmid (kan6) and any alterations in plasmid size are readily ascertained in SnaBI digested mutant DNA preps. Alterations in plasmid copy number are readily ascertained by comparisons of the relative intensities of plasmid bands in DNA preps of the parent B. japonicum 110 spc(kan6) and those of the mutant strains. Mutants which retained the plasmid and had no visible alteration in the size of the plasmid or plasmid copy number were selected for further characterization. Mutant classes I and III were eliminated by these criteria.

Mutants were cured of kan6 by inoculating 5 ml of Ag medium in the absence of antibiotics with a single colony and growing the culture to saturation. Cultures were diluted and plated on Ag medium and single colonies were picked to Ag and Ag+tetracycline (75 μg/ml). Tetracycline-sensitive plasmid-cured clones were selected and purified.

Regulation of the nodABC genes in the kan6 cured mutants was assessed to further characterize their properties. The nodC-lacZ fusion plasmid, pEA2-21, was introduced into the kan6 cured mutants by conjugation. Expression of β-galactosidase from the nodC-lacZ fusion reflects regulation of the nodABC genes. Assays of β-galactosidase activity were used to distinguish mutations on kan6 from mutations in the B. japonicum 110 chromosome. Curing of kan6 and introduction of pEA2-21 should result in a strain indistinguishable in regulation of expression of β-galactosidase from the parent 110spc(pEA2-21) in those cases where the mutation is on the kan6 plasmid. On the other hand, when the mutation is in the genome, curing of kan6 and introduction of pEA2-21 should result in a strain displaying altered regulation of the nod genes on pEA2-21 compared to that of 110spc(pEA2-21). Three plasmid-cured mutant strains designated 31c1, 32c1 and 46c1 carrying mutations on the genome which lead to increased streptomycin resistance in the absence of inducer were identified. These mutants represent class V of Table 1. In each case, the mutants carrying pEA2-21 produced both higher constitutive levels of β-galactosidase as well as much higher β-galactosidase levels on induction, as compared to the parent strain (Table 2).

Induction of β-galactosidase activity in strains 31c1(pEA2-21), 32c1(pEA2-21), 46c1(pEA2-21) and 110spc(pEA2-21) by various levels of daidzein was determined (FIG. 2). At the lowest level of daidzein tested (0.05 μM), the measured level of β-galactosidase in the mutants approached the maximal level attained by the parent 110spc (at 5.0 μM). At higher daidzein concentrations, each of the mutants had approximately 4 times the activity of the wild-type.

Induction of the nod genes by a variety of potential inducers was assessed (Table 3). Mutant 46c1(pEA2-21) is different from the other mutant strains in its significantly greater response to genistein biochanin A, formononetin and 4′,7-dihydroxyflavone To assay for β-galactosidase activity, exponentially growing cultures of strains containing the assay plasmid, pEA2-21, were incubated in the presence of inducers (5 μM), see Table 2. Inducers were added as ethanol solutions, or in the case of 4′,7-dihydroxyflavone, as a dimethylformamide (DMF) solution. In the case of addition of ethanol or DMF solutions of individual compounds, the final concentration of ethanol or DMF in the culture was always less than 2% (v/v) and an equivalent amount of ethanol or DMF was included with controls. Samples and controls were incubated at 28° C., after which aliquots were taken for β-galactosidase assay and measurement of culture turbidity (O.D. 600 nm).

The standard o-nitrophenyl-β-D-galactoside (ONPG) β-galactosidase assay of Miller (1972) Experiments in Molecular genetics, Cold Spring Harbor Press, Cold Spring Harbor, N.Y. was used. Samples were treated with chloroform-SDS to permeabilize cells, incubated with ONPG for up to two hours after which the absorbance of the sample was measured. The O.D. measurements were done at 410 nm and 630 nm rather than the standard 420 nm and 600 nm, so that an ELISA reader could be employed. The assay volume employed was 0.5 ml. β-galactosidase activity was expressed in "Miller units" (U), defined by the equation:

$$U = 1000 \times O.D.410 / V \times T \times O.D.630$$

where O.D. 410 is the absorbance at 410 nm, O.D. 630 is the absorbance at 630 nm (culture turbidity), V is the volume of culture mixed with buffer (total sample volume is 0.5 ml) and T is the time of incubation with ONPG in minutes.

Example 4

Symbiotic and Competitive Properties of the Mutants

Soybean plants (as 3–4 day germinated seedlings) were inoculated with approximately $2 \times 10^5$ cells of 31c1, 32c1, 46c1 or 110spc. After 28 days, nodule number, nodule mass and nitrogen fixation phenotype (as plant color) were assessed (Table 4). Mutant 32c1 made a normal number of small nodules that failed to fix nitrogen resulting in a yellow, stunted plant. Mutants 31c1 and 46c1 were indistinguishable from parent 110spc in number of nodules and nodule mass and nitrogen fixation phenotype.

Competitiveness of the mutant strains for nodulation was assessed relative to the parent 110 strain. Soybean plants were inoculated, as described above, with mixtures of the mutants and parent strain with a B. japonicum 110 spontaneous spectinomycin mutant. Three different ratios in combination with 110spc were employed. After 28 days, nodule occupancy was determined by crushing nodules and plating on Ag plates containing 250 μg/ml of either streptomycin or spectinomycin. Strains 31c1, 32c1, 46c1 and 110 spc are resistant to spectinomycin but sensitive to streptomycin while strain 110str is sensitive to spectinomycin but resistant to streptomycin. The results are presented in Table 5. Mutants 31c1 and 32c1 were Comp− with respect to the parent, while mutant 46c1 was Comp+ with respect to the parent.

Example 5

Comparison of Competitive Ability of a Brady-Rhizobium Japonicum USDA 110 Recombinant Strain Containing Constitutive NodABC Genes to that of the B. Japonicum Hyperinducible Mutants A B. japonicum USDA 110 recombinant having constitutively expressed nodABC genes was prepared by inserting a fragment of Tn5 containing the kanamycin resistance gene (kan) and its constitutive promoter upstream of ORF and the nodABC operon in the USDA 110 genome.

Briefly, the recombinant was constructed by insertion of an approximately 1.3 kb SalI-XhoI DNA fragment which contained a 20 bp SalI-SmaI polylinker sequence from pIC20H, the 1.3 kb SmaI-HindIII fragment of Tn5, a 32 bp HindIII-EcoRI sequence from pBR322 and a 20 bp EcoRI-XhoI polylinker sequence from pIC20H into the nodC-lacZ fusion plasmid pEA2-21. The kan fragment was inserted into a unique SalI site near the middle of nodD1 to produce the nodC-lacZ fusion plasmid pEA2-212 in which the nptII gene is oriented in the same direction as the downstream ORF and nodABC genes. When transferred into *B. japonicum* USDA 123, the β-galactosidase reporter gene from pEA2-212 was constitutively expressed to about the same level both in the presence and absence of daidzein. Expression in the presence of daidzein was not enhanced. The nodABC operon was apparently under the regulatory control of the constitutive nptII promoter sequences.

The nodD1/nptII insert region of pEA2-212 was then introduced into the genome of a *B. japonicum* USDA 110 spectinomycin (spc) resistant spontaneous mutant by recombination. An EcoRI fragment of pEA2-212 containing a portion of nodD1, kan and a portion of ORF was cloned into the suicide vector pSUP202 which can be transferred from *Eschericia coli* into *B. japonicum* strains, but cannot replicate in *B. japonicum*. Two recombinant clones, representing the two orientations of insertion, were isolated. In the clone designated 2A, the kan gene insert is positioned upstream and in the same orientation as the nodABC operon (see FIG. 3).

The competitive ability of the USDA 110 kan insertion mutant 2A was compared to that of a USDA 110 streptomycin mutant (str, spontaneous mutant) which contained a wild-type nod gene region. The results of competition experiments at two inoculum ratios on greenhouse grown soybean plants are shown in Table 6. Included as controls are mixtures of USDA 110spc with USDA 110str. The results shown in Table 6 indicate that constitutive expression of the nodABC genes in clone 2A does not enhance competitiveness. USDA 110spc, 110str and the 2A recombinant clone all produced a normal number of nodules, that fixed nitrogen when inoculated singly on soybean plants.

We claim:

1. A method for selecting a mutant of a parent Rhizobium or Bradyrhizobium legume-nodulating bacterium which is enhanced in competition for nodulation of a legume as compared to the parent legume-nodulating bacterium, which method comprises the steps of:
   i. screening a population of said parent legume-nodulating bacterium, which population contains mutants, for hyperinducible mutants by detection of hyperinducible phenotype, thereby selecting a set of hyperinducible mutants;
   ii. eliminating from said set of hyperinducible mutants those that do not fix nitrogen when inoculated on a legume by screening each hyperinducible mutant for its ability to fix nitrogen in planta, thereby producing a subset of said hyperinducible mutants;
   iii. selecting from said subset of hyperinducible mutants those which are more competitive for nodulation on said legume than said parent legume-nodulating bacterium by testing each mutant in said subset of hyperinducible mutants for competition in a nodule competency experiment using a mixed inoculum comprising a mutant in said subset and said parent legume-nodulating bacterium wherein enhanced competition is recognized by greater relative nodule occupancy of the mutant as compared with said parent strain, thereby selecting mutants of said parent legume-nodulating bacterium enhanced in competition for nodulation.

2. The method of claim 1, wherein said parent legume-nodulating bacterium is a strain of Rhizobium.

3. The method of claim 1, wherein said parent legume-nodulating bacterium is a strain of Bradyrhizobium.

4. The method of claim 3, wherein said parent legume-nodulating bacterium is a strain of *Bradyrhizobium japonicum*.

5. The method according to claim 1 wherein said screening step (i) comprises the steps of:
   i. conjugating a selection plasmid into said parent legume-nodulating bacterium, wherein said selection plasmid comprises an inducible nod gene-selectable marker gene translational fusion, thereby producing a selectable parent exconjugant strain of said legume-nodulating bacterium;
   ii. selecting mutants of said selectable parent exconjugant strain which constitutively express a phenotype of said nod gene-selectable marker gene translational fusion independently of the presence of a nod gene inducer in their growth medium, thereby selecting a set of constitutive mutants which constitutively express the selectable phenotype;
   iii. eliminating from said set of constitutive mutants those in which the constitutive selective phenotype is caused by a mutation of said selection plasmid by discarding those mutants which no longer express the constitutive selective phenotype when cured of said selection plasmid and after a selection plasmid is reintroduced; and also eliminating from said set of constitutive mutants those mutants which when cured of said selectable plasmid retain the constitutive selectable phenotype, thereby producing a subset of said constitutive mutants;
   iv. selecting from said subset of constitutive selectable mutants that have a hyperinducible nodulation phenotype by testing for an expression level of said selectable phenotype when said nod gene inducer is present in their growth medium which is higher than that of said selectable parent strain of said legume-nodulating bacterium, there producing a set of hyperinducible mutants of said parent legume-nodulating bacterium.

6. The method of claim 5, wherein said parent legume-nodulating bacterium is a strain of Rhizobium.

7. The method of claim 5, wherein said parent legume-nodulating bacterium is a strain of Bradyrhizobium.

8. The method of claim 7, wherein said parent legume-nodulating bacterium is a strain of *Bradyrhizobium japonicum*.

9. The method of claim 5, wherein said selectable marker gene is an antibiotic resistance gene.

10. The method of claim 9, wherein said antibiotic resistance gene is a streptomycin resistance gene.

11. The method of claim 5, wherein said inducible nod gene within the nod gene-selectable marker gene translational fusion is derived from the nodABC transcription unit of said parent legume-nodulating bacterium.

12. The method of claim 5, wherein said selectable parent exconjugant strain containing said selection plasmid is subjected to mutagenesis prior to selection of said set of constitutive mutants.

13. The method of claim 5, wherein said set of hyperinducible mutants is selected by the steps of:
   i. curing each of the hyperinducible nod gene mutants of said selection plasmid, thereby producing a set of cured hyperinducible mutants;
   ii. introducing into said set of cured hyperinducible mutants an assay plasmid which comprises an inducible nod gene-reporter gene fusion; and
   iii. selecting those-mutants which display a higher level of basal and induced expression of said inducible nod gene-reporter gene fusions compared to the level of expression of said inducible nod gene-reporter gene fusion of said parent legume-nodulating strain comprising said assay plasmid, thereby selecting a set of hyperinducible nod gene mutants.

14. The method of claim 13, wherein said inducible nod gene-reporter gene fusion comprises the lacZ gene.

15. A mutant of a strain of *Bradyrhizobium japonicum*, wherein said mutant has a hyperinducible phenotype, a Comp+ phenotype wherein said mutant fixes nitrogen in planta and wherein said mutant is *Bradyrhizobium japonicum* USDA 110 strain 46c1.

* * * * *

UNITED STATES PATENT AND TRADEMARK OFFICE
CERTIFICATE OF CORRECTION

PATENT NO. : 5,432,079
DATED : July 11, 1995
INVENTOR(S) : Eric Johansen, et al

It is certified that error appears in the above-indentified patent and that said Letters Patent is hereby corrected as shown below:

Column 2, line 3: Delete "(NOd$^+$)" and insert --(Nod$^-$)--.

Column 2, line 29: Delete "nod$^-$" and insert --Nod$^-$--.

Column 2, line 61: Delete "Russel" and insert --Russell--.

Column 3, line 41: Delete "node" and insert --nodE--.

Column 3, line 45: Delete "(1986)" and insert --(1985)--.

Column 3, line 59: Delete "980) Three" and insert --980). Three--.

Column 4, line 16: Delete "genes In" and insert --genes. In--.

Column 4, line 17: Delete "flavones:" and insert --flavones,--.

Column 4, line 44: Delete "nodD'" and insert --nodD$^-$--.

Column 6, line 63: Delete "sits" and insert --site--.

UNITED STATES PATENT AND TRADEMARK OFFICE
CERTIFICATE OF CORRECTION

PATENT NO. : 5,432,079
DATED : July 11, 1995
INVENTOR(S) : Eric Johansen, et al

It is certified that error appears in the above-indentified patent and that said Letters Patent is hereby corrected as shown below:

Column 7, lines 1-2: Delete "HindII" and insert --HindIII--.

Column 7, line 14: Delete "DptII" and insert --nptII--.

Column 16, lines 3-4: Delete "(O.D. 600 nm)." and insert --(O.D. at 600 nm).--

Signed and Sealed this

Sixteenth Day of January, 1996

BRUCE LEHMAN

Attest:

Attesting Officer

Commissioner of Patents and Trademarks